United States Patent
Florent

(12) 
(10) Patent No.: US 9,545,237 B2
(45) Date of Patent: Jan. 17, 2017

(54) METHOD AND DEVICE FOR RECORDING A VASCULAR STRUTURE DURING INTERVENTION

(75) Inventor: Raoul Florent, Ville D'Avray (FR)

(73) Assignee: Koninklijke Philips N.V., Eindhoven (NL)

(*) Notice: Subject to any disclaimer, the term of this patent is extended or adjusted under 35 U.S.C. 154(b) by 1578 days.

(21) Appl. No.: 12/527,935

(22) PCT Filed: Feb. 22, 2008

(86) PCT No.: PCT/IB2008/050646
§ 371 (c)(1),
(2), (4) Date: Aug. 20, 2009

(87) PCT Pub. No.: WO2008/104909
PCT Pub. Date: Sep. 4, 2008

(65) Prior Publication Data
US 2010/0063389 A1   Mar. 11, 2010

(30) Foreign Application Priority Data
Feb. 27, 2007   (EP) .................................... 07103145

(51) Int. Cl.
 *A61B 6/00*  (2006.01)
 *A61B 6/12*  (2006.01)
(52) U.S. Cl.
 CPC ................. *A61B 6/504* (2013.01); *A61B 6/12* (2013.01); *A61B 6/481* (2013.01)

(58) Field of Classification Search
 CPC ........... A61B 6/12; A61B 6/481; A61B 6/504; G01R 19/0084; H02M 2001/0009
 USPC ........................................................ 600/431
 See application file for complete search history.

(56) References Cited

U.S. PATENT DOCUMENTS

| 5,150,292 A | 9/1992 | Hoffmann et al. |
| 6,493,575 B1 * | 12/2002 | Kesten et al. ................ 600/431 |
| 6,597,938 B2 | 7/2003 | Liu |
| 2007/0269000 A1 * | 11/2007 | Partain et al. .................. 378/37 |
| 2008/0281205 A1 * | 11/2008 | Naghavi et al. ............... 600/458 |
| 2010/0035284 A1 * | 2/2010 | Buhimschi et al. ......... 435/7.92 |

FOREIGN PATENT DOCUMENTS

| JP | 2102209 A | 10/1988 |
| JP | 5023326 A | 10/1991 |
| JP | 7023938 A | 7/1993 |

(Continued)

OTHER PUBLICATIONS

The American Heritage Dictionary of the English Language, fifth Ed., (c)2015.*

(Continued)

*Primary Examiner* — James Kish
*Assistant Examiner* — Saurel J Selkin

(57) ABSTRACT

Method and device for recording a vascular structure during intervention comprises steps or elements for detecting S1 an injection of a contrast agent 6 provided to the vicinity of a device landmark 5, monitoring S3 for a predetermined time the vicinity of the device landmark 5, generating S3*a* time-contrast curves based on the monitored vicinity of the device landmark 5, analyzing S4*a* the time-contrast curves, and determining S4*b* a best instant as a visibility optimum based on the time-contrast curves.

13 Claims, 6 Drawing Sheets

(56) References Cited

FOREIGN PATENT DOCUMENTS

| JP | 2006506117 A | 11/2003 |
| JP | 2007021006 A | 7/2005 |
| WO | WO2004044847 | 5/2004 |
| WO | WO2005104951 | 11/2005 |
| WO | WO2006103644 | 10/2006 |

OTHER PUBLICATIONS

Bredno, J., et al., "Algorithmic Solutions for Life Device—Two-Vessel Match", Proceedings of SPIE, vol. 5370—Medical Imaging 2004: Imaging Processing, May 2004, pp. 1486-1497.

* cited by examiner

METHOD AND DEVICE FOR RECORDING A VASCULAR STRUTURE DURING INTERVENTION

FIELD OF THE INVENTION

The present invention relates to a method and device for recording a vascular structure during intervention, and particular to a method and device for recording a vascular structure during intervention, which may be used by an imaging system for PTCA (Percutaneous Transluminal Coronary Angioplasty) in catheter laboratories to treat cardiac stenosis.

BACKGROUND OF THE INVENTION

One of the most delicate phases during PTCA is the passing of a guide-wire tip through the targeted lesions (stenosis). The vessel walls at this location are usually uneven and, by definition, the conduct is narrowed. It follows that stenosis passing is one of the most time consuming (and therefore dose generating) parts of the intervention.

One of the reasons why the stenosis passing phase is difficult comes from the fact that it is achieved almost blindly and on a moving target. Most of the time, the physicist only sees the wire tip while trying to figure out what the stenosis looks like and what is the exact location of the tip within that stenosis. In this process, the physicist may either try to mentally register the current tips location with the stenosis visible in the angiogram, or he may inject a small shot of contrast agent.

A first approach that consists in comparing with the angiogram is difficult and bound to all sorts of inaccuracies, in particular due to the cardiac and respiratory motions.

A second approach that involves contrast agent injection is unfortunately very transitory and only offers a glimpse of the situation. It is also made difficult by the cardiac and respiratory motions.

A third solution would consist in using some kind of cardiac road mapping technique. This kind of solution does not yet exist on current intervention systems and is difficult to implement.

A description of a basic interventional procedure can be found in 'Algorithmic Solutions for Life Device—Two-Vessel Match', J. Bredno, B. Martin-Leung, K. Eck, in the proceedings of SPIE, Volume 5370-Medical Imaging 2004: Imaging Processing, J. Michael Fitzpatrick, Milan Sonka, Editors, May 2004, Pages 1486-1497. Accordingly, after a catheter is inserted into the vascular system at an access site, it is advanced along large vessels to the vascular structure that requires treatment. Contrast agent is injected via the catheter and cathlab X-ray equipment records an angiographic sequence that shows the vessels when filled with contrast agent. The diagnostic angiogram acquisitions can be repeated with varying imager geometries. Diagnosis and intervention planning are based on such diagnostic angiograms. During intervention, a flexible, partially or fully radial opaque guide-wire is advanced to the affected vascular structures, e.g. stenosis in coronaries, neurovascular aneurysms, or arterio-venous malformations. Fluoroscopic low-dose X-ray surveillance visualizes the guide-wire and allows for the hand-eye coordination of the interventionalist while advancing the guide-wire. When positioned, the guide-wire serves as rail to deliver interventional devices, e.g. balloons for dilation and stent delivery, detachable coils for aneurysm clotting. The delivery and deployment of the interventional devices is also fluoroscopic controlled.

SUMMARY OF THE INVENTION

It may be seen as an object of the present invention to improve the interventional situation and to offer a comfortable way to monitor the current stenosis-passing situation.

The object of the present invention is solved by the subject matter of the independent claims, wherein embodiments thereof are incorporated in the dependent claims.

According to an exemplary embodiment of the invention, a method for recording a vascular structure during intervention comprises detecting an injection of a contrast agent provided to the vicinity of a device landmark, monitoring for a predetermined time the vicinity of the device landmark, generating time-contrast curves based on the monitored vicinity of the device landmark, analyzing the time-contrast curves and determining a best instant as a visibility optimum based on the time-contrast curves.

Thus, the method is capable of automatically capturing and enhancing a view of a device landmark, e.g. a guide-wire tip or a stenosis balloon marker at a very instant when a contrast agent puff reaching the device landmark's surroundings produces optimal visualisation conditions. This automatic capturing and enhancing of the best instant is an advantageous feature at stenosis passing time. It makes the most of even the weakest contrast agent injection and offers a motion-free optimal view of, for example, a stenosis anatomy together with the exact location of the device landmark in form of, e.g. a tip at the capture instant. Thus, a kind of snapshot will bring to the physicist precious information elements that will help him to determine how to proceed with the intervention. As a matter of fact, the method may be used to all kind of markers and catheters, or even to anatomy landmarks like aneurysms. Further, the method solves the cardiac and respiratory motion issues.

According to an exemplary embodiment of the invention, the method further comprises visualizing the vicinity of the device landmark at the best instant.

Thus, for the physicist or user it is possible to get visualised the vicinity of the device landmark, wherein the vicinity should be understood as the area of interest with respect to the intervention.

According to an exemplary embodiment of the invention, the device landmark is a guide-wire tip or a stenosis balloon marker.

Thus, the method is applicable with devices using a guide-wire tip, for example, for implementing a stent, as well as apparatuses for interventions and treatment of stenosis by means of a stenosis balloon.

According to an exemplary embodiment of the invention, the method further comprises constantly detecting and locating the device landmark.

When using a device landmark, e.g. a guide-wire tip, having a high X-ray absorbing nature and a limited length, the detection process is fairly easy and may be undertaken with conventional ridge enhancement and thresholding techniques. This approach may even be underpinned by ridge tracking techniques.

According to an exemplary embodiment of the invention, the method further comprises monitoring a run with respect to detection of a contrast agent injection.

Thus, it is possible to provide a segmentation of the device landmark like a tip at each frame of a current fluoroscopic run.

According to an exemplary embodiment of the invention, the method further comprises outputting a result of detection as a Boolean indicator.

Thus, it is possible to have a clear indication on whether a contrast agent is injected or not. It should be noted that a run may be monitored for the detection of possible contrast injection, wherein for this detection task a non-image-based device may be involved, like an electric injector command, which may be monitored, as well as purely image-based techniques. A relative sudden increase of the average ridgeness along the run is a typical way of achieving this detection.

According to an exemplary embodiment of the invention, the method further comprises monitoring grey-level values around the device landmark.

The detection of a contrast agent injection triggers the monitoring. Once a contrast agent has been produced through the injection catheter it rapidly reaches the vicinity of the device landmark, e.g. a guide-wire tip. The continuous segmentation of the device landmark provides the geometry of the area where contrast is to be looked for and analyzed. By monitoring grey-level values around and on the device landmark, a producing or generating of several time-intensity or time-contrast curves is possible, for example, one curve for the average grey-level on a tip over the time, and one curve for the average on both sides of the device landmark.

According to an exemplary embodiment of the invention, the method further comprises computing a visibility index for the device landmark and its surrounding.

The time-intensity or time-contrast curves are analyzed and a visibility index for the device landmark and its surrounding and vicinity, respectively, is computed, wherein the instant at which this index reaches an optimal value determines the so-called best instant.

According to an exemplary embodiment of the invention, the method further comprises determining the best instant when detecting an injection of contrast agent hiding the device landmark as an instant at a time immediately before or after hiding the device landmark, otherwise at a time of maximum contrast agent concentration.

Typically, two situations might occur. In the first situation, a large amount of contrast agent is injected. In this case, the device landmark will at some stage be completely hidden by the contrast agent, and the best instant is either a little bit before this situation occurs or a little bit after, when the contrast agent flushes away. In the second situation, only a limited amount of contrast agent is injected. In this case, the maximum contrast agent concentration around the tip leaves the tip clearly visible, and also produces the best visibility for the stenosis. In other words, when injecting a large amount of contrast agent, only the vessel, the vascular structure, or stenosis, respectively, are visible, wherein, when injecting no contrast agent only the device landmark, e.g. the tip, is visible. It therefore corresponds to the best instant, when a combination of the vessel, the vascular structure, or stenosis, respectively, and the device landmark, e.g. the tip is at an optimum visibility.

According to an exemplary embodiment of the invention, the method further comprises determining the visibility optimum where the device landmark and a lesion have an optimum contrast correlation over the background.

Thus, the best instant corresponds to some visibility optimum where both the device landmark and the lesion stand out clearly against the background. It should be noted that an optimum contrast correlation means an optimum with respect to a clear visibility of the device landmark and the lesion, for example, a tip of a guide-wire and the stenosis over the background, wherein this optimum is not limited to a maximum contrast of either the device landmark or the lesion, respectively, over the background, but may be also an optimum allowing the best visibility of the device landmark as well as the lesion at the same time over the background.

According to an exemplary embodiment of the invention, the method further comprises visualizing the vicinity of the device landmark together with a lesion.

Thus, it is possible for the interventionalist to get an expression on the area of interest of the intervention, that means the geometry of the device landmark and lesion, for example, the position of a guide-wire tip and a stenosis, to each other.

According to an exemplary embodiment of the invention, the method further comprises visualizing of a zoomed area of interest.

This may provide an even neater visualisation. It should be noted that, of course, all sort of spatial and temporal filters may be applied, together with histogram manipulations.

According to an exemplary embodiment of the invention, the method further comprises displaying a visualisation on a secondary monitor.

Thus, for example, the enhanced and zoomed view of the lesion and the device landmark, e.g. the stenosis plus tip, may be displayed on a dedicated monitor wherein this view will typically be hold until a new contrast agent puff is injected, thus updating the view.

It should be noted that the described method is fully automatic and does not require any manual interaction.

It should be noted that the above described exemplary embodiments of the invention apply also for the device, the programme product and the computer readable medium.

It may be seen as a gist of the present invention to provide a possibility for optimum visualisation of a device landmark like a guide-wire tip and a lesion like a stenosis, and at the same time to avoid bad visualisation due to low or high contrast agent concentration in the vicinity of the device landmark. In addition, because it optimises visualisation, the invention has the effect of reducing the amount of necessary contrast agent. This contrast agent reduction is important both for cost reduction reasons and also for the patient's heath, since an excess of contrast agent may have negative renal impacts.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EXEMPLARY EMBODIMENTS

Figure 1:
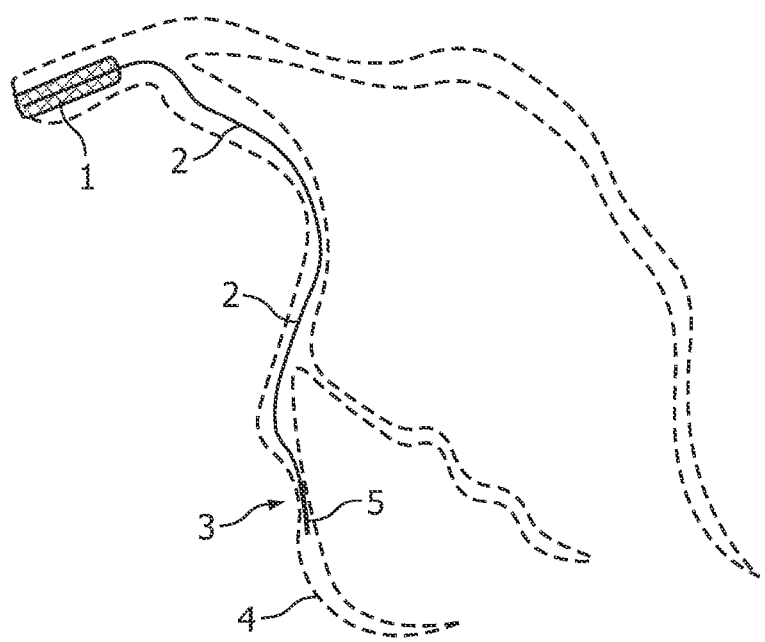
FIG. 1 illustrates a geometry of a vessel, guide-wire and tip before an injection

FIG. 1 illustrates a geometry of a vessel or generally a vascular structure, in which an injection catheter 1 is inserted. A guide-wire tip 5 is conducted by a guide-wire 2 in order to examine and treat a stenosis 3 at a coronary artery 4. It should be noted that the coronary artery 4 is in fact invisible. The guide-wire tip 5 is illustrated as a darker segment, and may be designed to be detectable by a common X-ray examination, wherein the guide-wire may be opaque with respect to X-ray radiation. Thus, the location of the guide-wire tip 5 may be detected by means of X-ray, wherein it is difficult to illustrate the stenosis 3, since the coronary artery generally is invisible with respect to X-ray radiation. Therefore, a contrast agent may be provided via the injection catheter in order to increase the contrast of the vascular structure, in particular the coronary artery including the stenosis 3.

Figure 2:
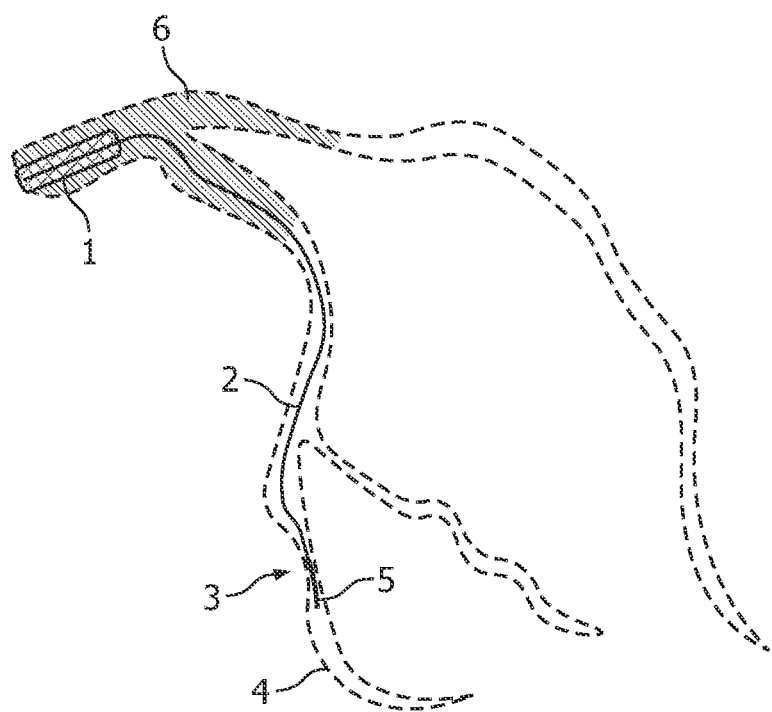
FIG. 2 illustrates a state in which a contrast agent injection has started, but the optimal instant is not yet reached

FIG. 2 illustrates a state in the vascular structure in which a contrast agent injection has started. The contrast agent has a limited propagation velocity, so that the contrast increases over the time.

In the example illustrated in FIG. 2, the contrast agent 6 propagates among others along the guide-wire, but presently did not reach the guide-wire tip, so that the contrast in the vicinity of the guide-wire tip 5 and the stenosis 3 presently is not sufficient for further investigations by X-ray radiation.

Figure 3:
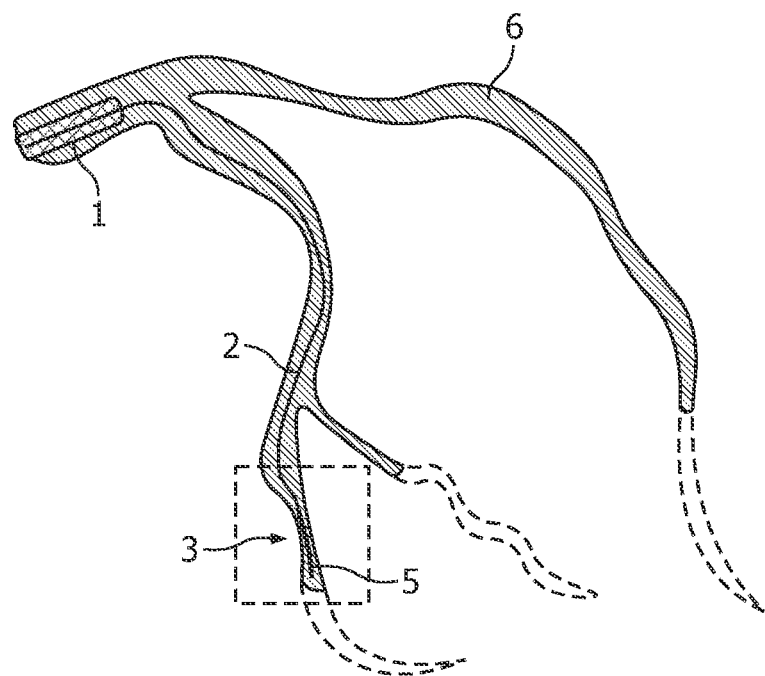
FIG. 3 illustrates a state in which the optimal instant is detected

In a further propagated state after a predetermined time the contrast agent further propagates along the guide-wire, as illustrated in FIG. 3. It should be noted that the contrast agent 6 also propagates along other vessels without a guide-wire, since the propagation of the contrast agent does not relate to the presence of the guide-wire.

In the state illustrated in FIG. 3, the contrast agent 6 has reached the guide-wire tip 5 and the stenosis 3. It should be noted that the concentration of the contrast agent 6 has a distribution over the location, and physically does not constitute a Boolean state. It should be noted that the propagation of the contrast agent 6 in FIGS. 2, 3 and 4 therefore only illustrates a kind of threshold, so that the illustration contains information with respect to a threshold concentration of the contrast agent. Due to the propagation of the contrast agent, the front of the slope continuously increases over the time, so that it is possible to detect an optimal instant, in which the concentration of the contrast agent is at an optimum for the investigation or the intervention by assistance of X-ray radiation.

According to an exemplary embodiment, it is possible to record over a predetermined range of time a plurality of pictures in order to determine the optimum instant by analyzing the recorded pictures. Thus, the illustration may be not in real time, but allows a determination of an optimal instant and an optimum illustration of the geometry of the stenosis. It should be noted that the geometry of the stenosis, and in particular the shape of the vessel walls, generally does not change to a large extent, so that a non real time illustration does not constitute a drawback for the inventive method.

Figure 4:
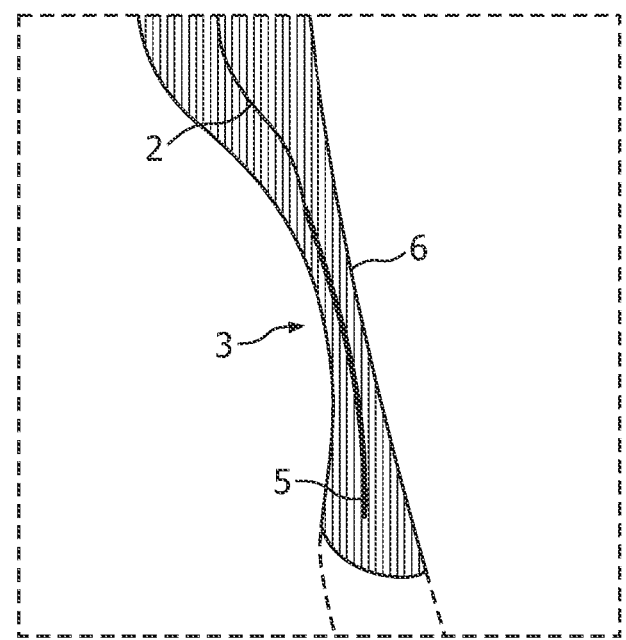
FIG. 4 is an enlarged illustration of the dashed square of FIG. 3 illustrating a stenosis and a tip at the optimal instant

FIG. 4 illustrates an enlarged view of the stenosis of FIG. 3. When interpreting the propagation of the contrast agent as illustrated in FIGS. 2, 3 and 4 as a particular threshold, the state illustrated in FIG. 4 is a state in which the guide-wire tip 5 within the stenosis 3 is close to an optimal instant, since the contrast agent 6 concentration exceeds, for example, a minimum threshold in the total environment of the guide-wire tip 5.

Figure 5:
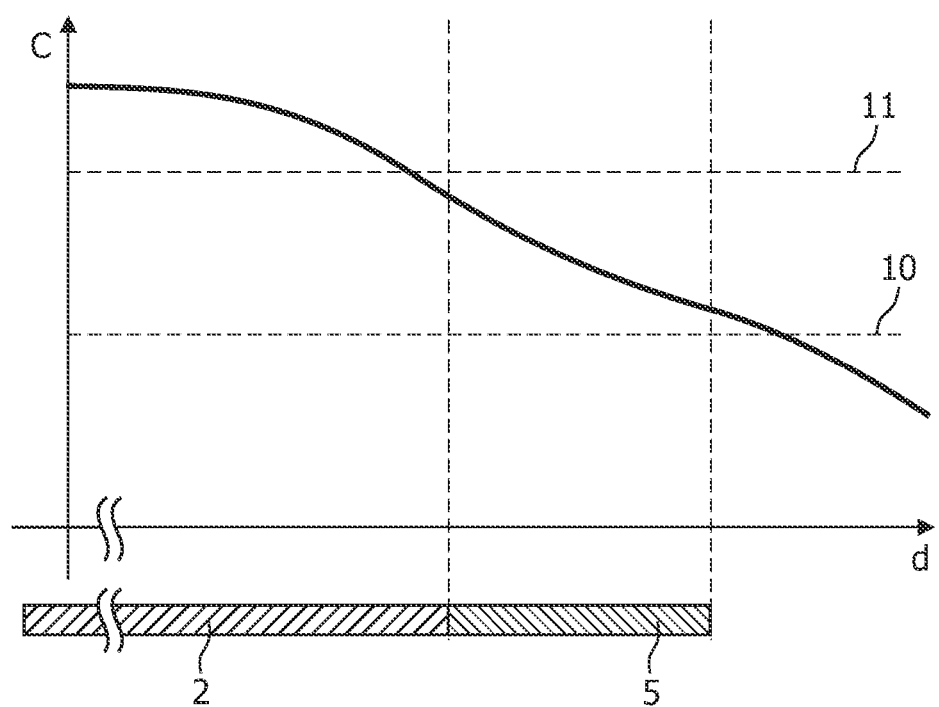
FIG. 5 illustrates a contrast agent concentration over a area of interest

FIG. 5 illustrates a distribution of the concentration C of the contrast agent 6 over the geometry close to the guide-wire tip 5 or the distance d. The concentration increases over the time so that at a particular instant depicted in FIG. 5, the concentration of the contrast agent exceeds a particular threshold 10 allowing to visualize of the vessel or stenosis. In this instant the concentration did not reach a maximum level 11 in the area of interest of the concentration C which maximum level concentration would hide the device landmark, e.g. tip 5. The area of interest is considered as the area of the tip in this exemplary embodiment. In other words, in the present exemplary embodiment the best instant occurs when in the area of the tip the concentration exceeds the threshold 10, but remains below a maximum or hiding level 11.

Figure 6:
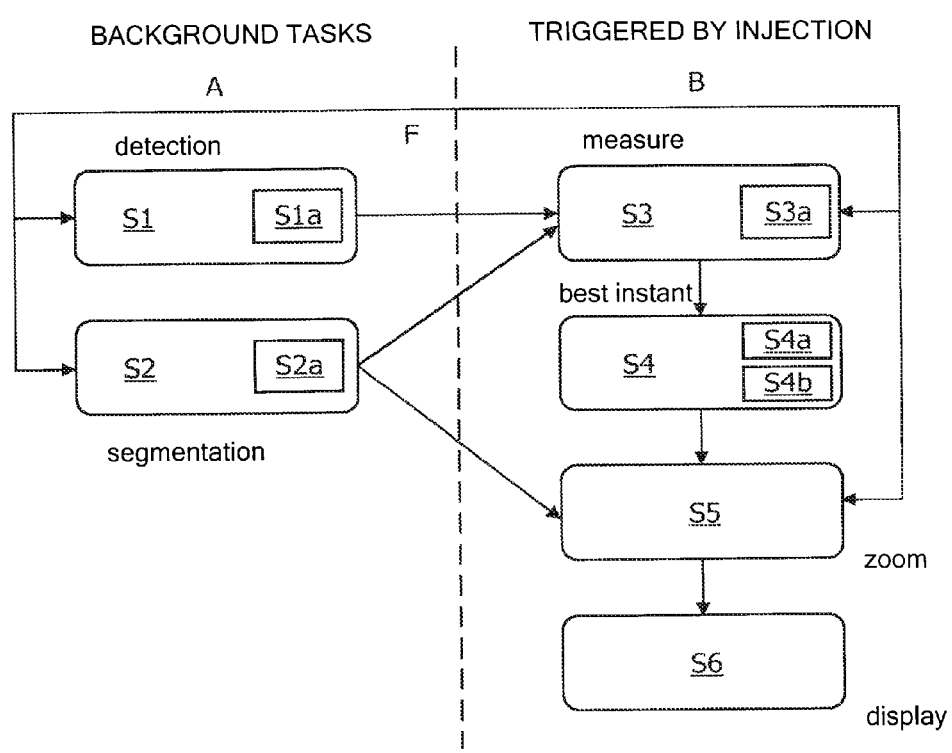
FIG. 6 is a flowchart of an exemplary embodiment of the inventive method

FIG. 6 illustrates an exemplary embodiment of the inventive method, wherein on the one side A background tasks are listed, and on the other side B aspects are listed, which are triggered by injection.

On a fluoroscopy run F a contrast agent injection detections S1 takes place as a background task, as well as a tip segmentation S2. A contrast measure around the tip S3 takes place triggered by the injection followed by a best instant computing S4, an enhancement and zoom S5 and a display in a dedicated monitor S6.

As a background task, the guide-wire tip is detected S1, in particular constantly detected S1a and located during, for example, a tip segmentation or tip location S2. Thanks to its very high X-ray absorbing nature and its limited length, this detection process is fairly easy and may be undertaken with conventional ridge enhancement and thresholding techniques. This approach may even be underpinned by ridge tracking techniques. In any case, this background task is to provide a segmentation of the tip at each frame of the current fluoroscopy run C.

As a further background task, a contrast agent injection detection S1 takes place. At the same time, the run is monitored S3 for the detection of a possible contrast injection. Of course, non-image-based devices could be involved for this detection task, explicitly electric injector command monitoring, but if this turns out to be non practical, one might resort to purely image-based techniques. A relative sudden increase of the average ridgeness along the run is a typical way of achieving this detection. The output of the step is for each image of the current fluoroscopy run a simple injection Boolean indicator S1a. Further, a tip segmentation S2 may take place.

Triggered by the injection, a contrast agent measurement around the tip S3 takes place. The detection of contrast agent triggers the remainder of the procedure. Once a contrast has been produced through the injection catheter, it rapidly reaches the tip vicinity, wherein the tip may be also any landmark as a marker on a stent or a catheter balloon. The continuous segmentation of the tip provides the geometry of the area where contrast is to be looked for and analyzed. Typically, the grey-level values around and on the tip are monitored S3a, thus producing S3a several time-intensity curves or time-contrast curves, for example, a first curve for the average grey-level on the tip along the time t, and a second curve for the average of both sides of the tip. The combination of the first curve and the second curve leads to the determination of a tip-over-surrounding contrast curve Ca. Likewise, a third curve for the average of the grey-levels on either side of the vessel, that is, at a certain distance from the tip can be determined. The combination of the second curve and the third curve leads to the determination of a vessel-over-surrounding contrast curve Cb. The contrast may also be interpreted as the intensity. The tip's vicinity may be interpreted as an area relevant for the intervention.

Figure 7:
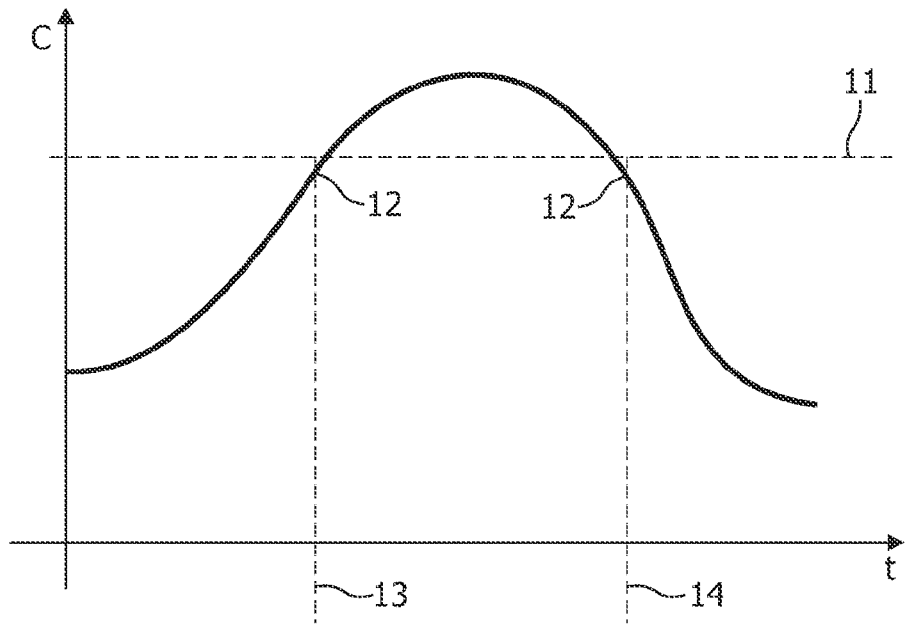
FIG. 7 illustrates a contrast agent concentration in a first mode
Figure 8:
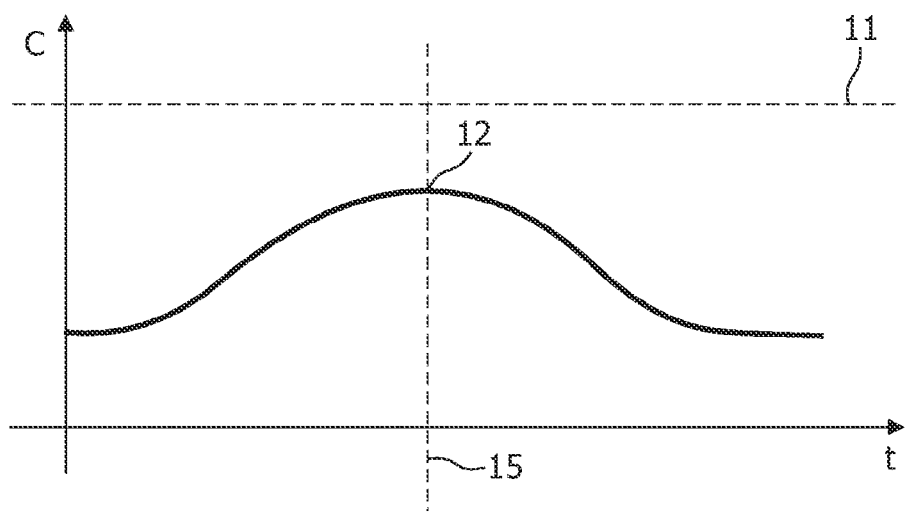
FIG. 8 illustrates a contrast agent concentration in a second mode
Figure 9:
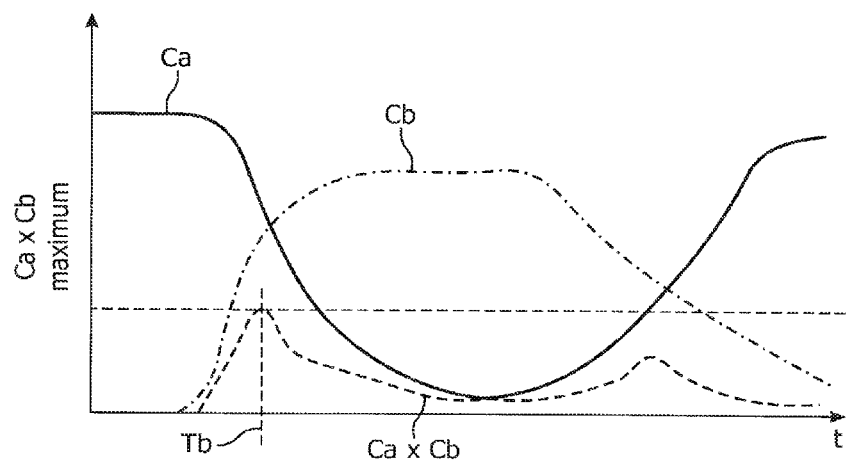
FIG. 9 illustrates a determination of a best instant

Afterwards, a determination of the best instant S4 takes place. The aforementioned time-contrast or time-intensity curves are analyzed S4a and a visibility index of the tip or a landmark and its surrounding is computed. In particular, this time-dependent index may be deduced from a combination of the contrast curves Ca and Cb in FIG. 9, which is illustrated as Ca×Cb and constitutes the visibility index for both the tip and the vessel. The instant at which this index reaches an optimal value determines S4b the so-called best instant. This is in FIG. 9 illustrated as the maximum of Ca×Cb at the time Tb. Typically, two situations might occur depicted in FIG. 7 and FIG. 8 as he concentration C on a predetermined location, e.g. the tip, over the time t. In the first one, a large amount of contrast agent is injected. In this case, the tip will at some stage be completely hidden by the contrast agent, and the best instant 12 is either a little bit before this situation occurs 13 or a little bit after 14, when the contrast agent flushes away. In the second situation, only a limited amount of contrast agent is injected. In this case, the maximal contrast agent concentration 15 around the tip or the landmark leaves the tip or landmark clearly visible, e.g. the concentration remains below the maximum visibility level 11, and also produces the best visibility for the stenosis 3. In other words, in the presence of too much contrast agent, i.e. the contrast agent concentration is high, only the vessel, vascular structure or stenosis is visible, since the high concentration of contrast agent hides the tip or the landmark. In presence of no contrast agent, only the device landmark or the tip is visible, however, the vessel, vascular structure or stenosis cannot be seen due to the missing presence of contrast agent, as depicted in FIG. 5. Therefore, an optimum between the two cases corresponds to the best instant. In both situations, the best instant corresponds to some visibility optimum, where both the tip and the lesion stand out clearly against the background, so that an optimum contrast correlation is available.

FIG. 9 further illustrates the best instant determination. In this figure, the tip-over-surrounding contrast curve Ca is represented together with the vessel-over-surrounding contrast curve Cb. FIG. 9 shows that Ca is maximum when no contrast agent is present around the tip. When contrast agent reaches the tip's surrounding, the tip's contrast decreases. On the contrary, the vessel-over-surrounding contrast is null when no contrast is present since the vessel are then transparent. When the contrast agent reaches the vessel next to the tip, the vessel contrast increases. Now, as an example, FIG. 9 illustrates the computing of the time-dependent visibility index as the product of Ca by Cb. FIG. 9 clearly shows that a maximum of this index curve can be found, thus determining the best instant. But the product of Ca and Cb, Ca×Cb, is only an example. Of course the product is only high when both Ca and Cb is high. It is therefore adapted to the invention goal to maximise the visibility of both the tip and the vessel. But other combinations are possible.

Afterwards, an enhancement and a zooming phase S5 takes place, in which the lesion together with the device landmark or tip partly visualised at the best instant. However, many enhancement techniques may be involved to make this visualisation even neater. Of course, one may zoom in on the area of interest, but all sort of spatial and temporal filters may be applied, together with histogram manipulations.

Finally, an automatic display on a secondary screen or any other appropriate illustration medium S6 takes place. Thus, the enhanced and zoomed view of the lesion plus device landmark or tip may be displayed on a dedicated monitor. This view will typically be held until a new contrast agent puff is injected, thus updating the view.

Figure 10:
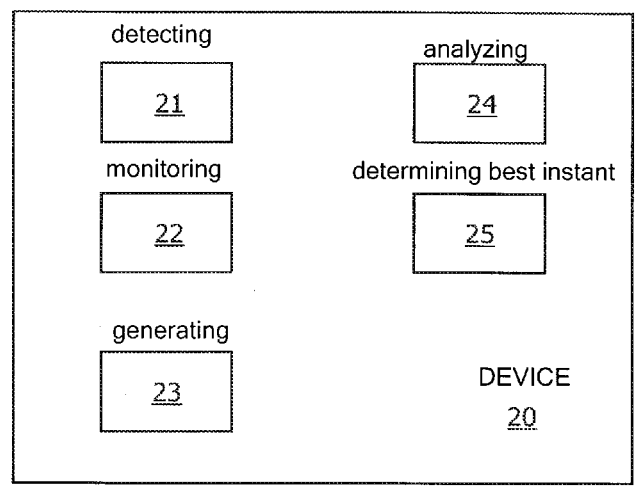
FIG. 10 illustrates a device according to en exemplary embodiment of the invention

FIG. 10 illustrates a device 20 according to en exemplary embodiment of the present invention including a detecting unit 21 adapted to detect an injection of a contrast agent provided to the vicinity of a device landmark, a monitoring unit 22 adapted to monitor for a predetermined time the vicinity of the device landmark, a generating unit 23 adapted to generate time contrast curves based on the monitored vicinity of the device landmark, an analyzing unit 24 adapted to analyze the time contrast curves, and a determining unit 25 adapted to determine a best instant as a visibility optimum based on the time contrast curves.

The described method is fully automatic and does not require any manual interaction.

It should be noted that also other situations could benefit from the inventive method. This could involve other devices, markers, catheters, coils, etc. and other kinds of anatomical landmarks, for example, aneurysms. More generally, an identifiable area of interest is to be determined, either automatically as in the case of the tip or landmark, or even thanks to provided indications, as in the case of a manually selected area. Then, triggered by the detection of a contrast agent injection, visibility measurements within the area would be computed, and the best instant may be determined. An optimal view of the best instant would then be computed.

A contrast agent injection may be image-based, or may be derived from an external indication, for example, in the case of an electrical contrast agent injector. The determination of the area of interest may be achieved in many different ways, by detection, tracking, correlation, etc. A variety of criteria may be envisioned for the computing of the best instant. Not only a frozen image but also a short enhanced run around the best instant may be displayed. In that case, motion compensated techniques could even be applied to cancel the motion problem. Not only cardiac, but also vascular and neuro interventions could be targeted.

This may be extended to all X-ray interventions, but even may be to other modalities relying on some sort of contrast agent like Magnetic-Resonance Imaging (MRI), Computer Tomography (CT), Ultrasound imaging(U/S).

It should be noted that the invention may be applied to a stenosis interventional process when setting a stent as well as a treatment of a balloon.

It should be noted that also other situations may benefit from the invention. This may involve other devices like markers, catheters, coils, etc and other kind of anatomical landmarks, for example, aneurysms.

It should be noted that the term 'comprising' does not exclude other elements or steps and the 'a' or 'an' does not exclude a plurality. Also elements described in association with the different embodiments may be combined.

It should be also noted that the reference signs in the claims shall not be construed as limiting the scope of the claims.

The invention claimed is:

1. A method for vascular intervention, comprising
triggering an injection of a contrast agent provided to the vicinity of a device landmark;
imaging the vicinity of the device landmark for a predetermined time after the trigger;
displaying an image of the vicinity of the device landmark;
generating during the predetermined time after the trigger a tip-over-surrounding and a vessel-over-surrounding time-contrast curves based on the monitored vicinity of the device landmark;
computing a time-dependent visibility index curve from the tip-over-surrounding and vessel-over-surrounding time-contrast curves, wherein the time-dependent visibility index curve has a maximum, thereby determining a best instant for visibility; and
holding the displayed image of the vicinity of the device landmark at the best instant until the next trigger injection of the contrast agent;
wherein the best instant is the time at the maximum of the time-dependent visibility index curve which is the product of the tip-over-surrounding and vessel-over-surrounding time-contrast curves; wherein the tip-over-surrounding time-contrast curve combines an average grey level on the tip and an average grey level on both sides of the tip; and wherein the vessel-over-surrounding time-contrast curve combines an average grey level on both sides of the tip with grey levels on a side of the vessel away from the tip.

2. The method of claim 1, wherein the device landmark is a guide wire tip or a stenosis balloon mark.

3. The method of claim 1, further comprising constantly detecting and locating the device landmark.

4. The method of claim 1, further comprising imaging a fluoroscopic run of a vascular intervention with respect to detection of a contrast agent injection.

5. The method of claim 1, further comprising outputting a visibility index curve as a Boolean indicator.

6. The method of claim 1, further comprising monitoring gray-level values around the device landmark.

7. The method of claim 1, further comprising displaying the image of the vicinity of the device landmark together with a lesion.

8. The method of claim 1, further comprising displaying an image of a zoomed area of interest.

9. The method of claim 1, further comprising displaying the image on a secondary monitor.

10. A non-transitory computer-readable medium having stored thereon instructions for performing the steps of:
triggering an injection of a contrast agent provided to the vicinity of a device landmark in a vascular intervention;
imaging the vicinity of the device landmark for a predetermined time after the trigger;
displaying an image of the vicinity of the device landmark;
generating during the predetermined time after the trigger a tip-over-surrounding and a vessel-over-surrounding time-contrast curves based on the monitored vicinity of the device landmark;
computing a time-dependent visibility index curve having a maximum from the tip-over-surrounding and vessel-over-surrounding time-contrast curves, thereby determining a best instant for visibility; and
holding the displayed image of the vicinity of the device landmark at the best instant until the next trigger injection of the contrast agent;
wherein the best instant is the time at the maximum of the time-dependent visibility index curve which is the product of the tip-over-surrounding and vessel-over-surrounding time-contrast curves; wherein the tip-over-surrounding time-contrast curve combines an average grey level on the tip and an average grey level on both sides of the tip; and wherein the vessel-over-surrounding time-contrast curve combines an average grey level on both sides of the tip with grey levels on a side of the vessel away from the tip.

11. The non-transitory computer-readable medium of claim 10, wherein the device landmark is a guide wire tip or a stenosis balloon mark.

12. A device for vascular intervention, comprising
a detector that triggers an injection of a contrast agent provided to the vicinity of a device landmark;
a fluoroscope that obtains grey level values in the vicinity of the device landmark for a predetermined time after the trigger;
a fluoroscope processor that processes a tip-over-surrounding time-contrast curve and a vessel-over-surrounding time-contrast curve based on the grey levels obtained in imaging of the vicinity of the device landmark during the predetermined time after the trigger and that computes a time-dependent visibility index curve having a maximum from the tip-over-surrounding and vessel-over-surrounding time-contrast curves, thereby determining a best instant for visibility; and
a display that holds a displayed image of the vicinity of the device landmark at the best instant until the next trigger injection of the contrast agent;
wherein the best instant is the time at the maximum of the time-dependent visibility index curve which is the product of the tip-over-surrounding and vessel-over-surrounding time-contrast curves; wherein the tip-over-surrounding time-contrast curve combines an average grey level on the tip and an average grey level on both sides of the tip; and wherein the vessel-over-surrounding time-contrast curve combines an average grey level on both sides of the tip with grey levels on a side of the vessel away from the tip.

13. The device of claim 12, wherein the device landmark is a guide wire tip or a stenosis balloon mark.

* * * * *